United States Patent [19]

Kitahara

[11] 4,116,637

[45] Sep. 26, 1978

[54] BLOOD SERUM APPLICATOR

[75] Inventor: Tomohiro Kitahara, Hachiouji, Japan

[73] Assignee: Olympus Optical Co., Ltd., Japan

[21] Appl. No.: 759,557

[22] Filed: Jan. 14, 1977

[30] Foreign Application Priority Data

Jan. 16, 1976 [JP] Japan .................................. 51/2499

[51] Int. Cl.² .......................... B01L 3/00; G01N 1/12;
G01N 31/06; G01N 33/16
[52] U.S. Cl. ................................ 422/63; 73/425.4 R;
422/100
[58] Field of Search .................................. 23/292, 259;
73/425.4 P, 425.4 R, 64.1, 61.1 C; 33/32 R, 41

[56] References Cited

U.S. PATENT DOCUMENTS

| 2,863,319 | 12/1958 | Molin | 23/292 X |
| 2,868,020 | 1/1959 | Williams, Jr. | 73/425.4 P UX |
| 3,505,858 | 4/1970 | Kohn | 73/61.1 C |
| 3,616,387 | 10/1971 | Siebert et al. | 73/61.1 C UX |

Primary Examiner—Morris O. Wolk
Assistant Examiner—Michael S. Marcus
Attorney, Agent, or Firm—Cushman, Darby & Cushman

[57] ABSTRACT

A blood serum applicator means for electrophoresis comprising two thin plates each having a narrow horizontal portions supported by a vertical supporting portion or portions and arranged with a pre-determined space between each other. Blood serum is permeated into a groove formed by both narrow horizontal portions and applied to a film such as filter paper, cellulose acetate film, etc. by pushing the above narrow horizontal portions onto the film.

5 Claims, 14 Drawing Figures

FIG. 1 FIG. 2 FIG. 3 FIG. 4
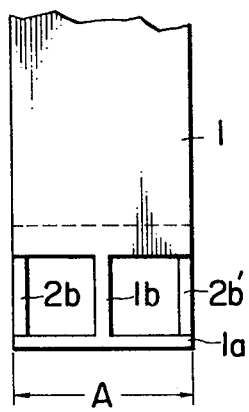
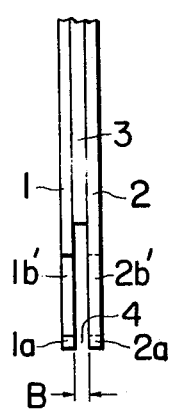
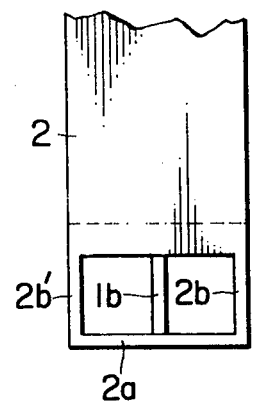
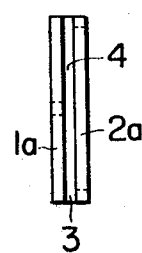
FIG. 5 FIG. 6 FIG. 7 FIG. 8
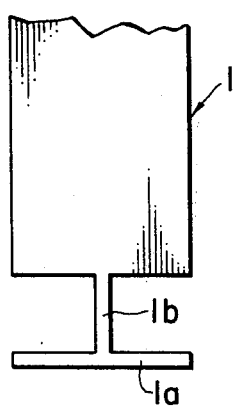
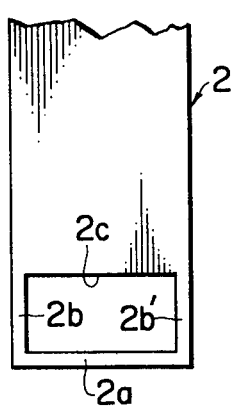
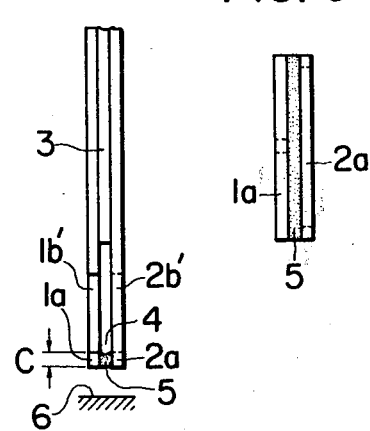

BLOOD SERUM APPLICATOR

BACKGROUND OF THE INVENTION (a) Field of the invention

The present invention relates to a blood serum applicator and, more particularly, to a blood serum applicator to be used in electrophoresis of blood serum for analysis of blood serum proteins etc.

(b) Description of the prior art

To analyze blood serum proteins etc. by electrophoresis, blood serum specimen taken from the patient is applied onto a film such as a filter paper, cellulose acetate film or the like (hereinafter referred to as film) and energized through the film so that a fractionated pattern of specimen is formed. If the blood serum applied onto the film at that time is not in a uniform straight line, it is impossible to obtain a sharp fractionated pattern of specimen and, consequently, it is impossible to analyze the blood serum correctly.

In the known method for applying the blood serum onto the film, blood serum is sucked into a micropipette and a line of blood serum is drawn on the film by using the micropipette. In such method, however, it is very difficult to apply the blood serum in a uniform and straight line and, moreover, it is very inefficient.

SUMMARY OF THE INVENTION

It is, therefore, a primary object of the present invention to provide a blood serum applicator in which two thin plates each having a narrow horizontal portion at its one end are held with a pre-determined space between each other by means of spacer and which is arranged to permeate the blood serum into a groove formed to the two narrow horizontal portions and then to apply the blood serum onto the film by pushing the narrow horizontal portions onto the film.

Another object of the present invention is to provide a blood serum applicator in which two thin plates each having a narrow horizontal portion at its one end are held with a predetermined space between each other by means of a spacer and in which one end of each narrow horizontal portion is partially cut so that surplus blood serum will not permeate when the blood serum is permeated into the groove formed by the two narrow horizontal portions.

BRIEF DESCRIPTION OF THE DRAWINGS

FIG. 1 shows a front view of a first embodiment of the blood serum applicator according to the present invention;

FIG. 2 shows a side view of the first embodiment;

FIG. 3 shows a back view of the first embodiment;

FIG. 4 shows a bottom view of the first embodiment;

FIG. 5 shows a front view of a first thin plate constituting the first embodiment;

FIG. 6 shows a front view of a second thin plate constituting the first embodiment;

FIG. 7 shows a side view of the first embodiment in the state that the blood serum is permeated;

FIG. 8 shows a bottom view of the first embodiment in the state that the blood serum is permeated;

DETAILED DESCRIPTION OF THE PREFERRED EMBODIMENTS

Figure 9:
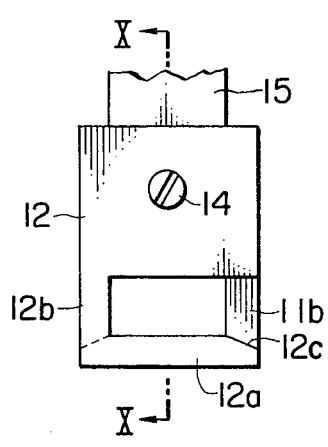
FIG. 9 shows a front view of a second embodiment of the present invention.

In the following, the concrete content of the present invention is described referring to respective embodiments shown on the accompanying drawings. FIGS. 1 through 4 respectively show a front view, side view, back view and bottom view of a first embodiment of the blood serum applicator according to the present invention. In these figures, numeral 1 designates a first thin plate, numeral 2 designates a second thin plate, and numeral 3 designates a spacer. Out of them, the first thin plate 1 has a narrow horizontal portion 1a and a vertical supporting portion 1b, which supports the narrow horizontal portion 1a, and they form a T shape as shown in FIG. 5. The second thin plate 2 has a cut portion 2c of, for example, rectangular shape near its one end as shown in FIG. 6 to form a narrow horizontal portion 2a and vertical supporting portions 2b and 2b' which support the narrow horizontal portion 2a. The blood serum applicator according to the first embodiment of the present invention is constructed by combining the first and second thin plates 1 and 2. The horizontal portions 1a and 2a form a linear groove of length A, width B and depth C between them as shown in FIGS. 1, 2 and 7. The shapes of vertical supporting portions 1b, 2b and 2b' of the first and second thin plates 1 and 2 are not limited to those shown in figures. Other shapes may be adopted on condition that the vertical supporting portion or portions of the first thin plate 1 do not become directly opposed to the vertical supporting portion or portions of the second thin plate 2 when the first and second thin plates are combined with each other.

Now, the blood serum applying operation by using the blood serum applicator according to the present invention is described below.

At first, the narrow horizontal portions 1a and 2a are dipped into the blood serum. Thus, the blood serum 5 permeates into the groove 4 as shown in FIGS. 7 and 8 because of capillarity. When the narrow horizontal portions in the above stated is pushed onto a film 6, it is possible to apply the blood serum 5 onto the film 6 in the form of straight line. As explained in the above, the blood serum applying operation by using the blood serum applicator according to the present invention is extremely simple compared with the known method employing a micropipette.

In the blood serum applicator according to the present invention, the vertical supporting portion 1b of the first thin plate 1 is not directly opposed to the vertical supporting portions 2b and 2b' of the second thin plate 2 and, therefore, capillarity does not occur at the vertical supporting portions. In other words, the blood serum 5 is permeated only into the groove 4 which is formed between narrow horizontal portions 1a and 2a. When the length A, width B and depth C are decided adequately, it is therefore possible to permeate the blood serum 5 always by the pre-determined amount accurately. Moreover, as the groove 4 is formed to have a uniform width and uniform depth along its whole length, the blood serum 5 is permeated uniformly along the whole length of the groove 4. Therefore, when the blood serum is applied by using the blood serum applicator according to the present invention, the applied blood serum always becomes uniform in its volume and shape.

Figure 10:
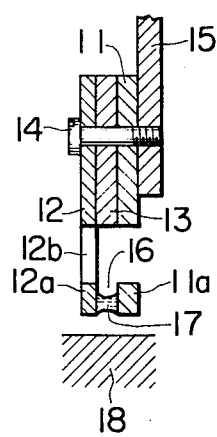
FIG. 10 shows a sectional view taken along the line X—X in FIG. 9.
Figure 11:
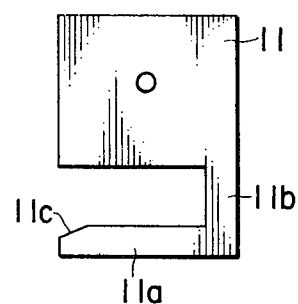
FIG. 11 shows a front view of a thin plate constituting the second embodiment.

Now, FIGS. 9 through 11 show a second embodiment of the blood serum applicator according to the present invention. In these figures, numerals 11 and 12 respectively designate a first and second thin plates which have the shape as shown in FIG. 11. In contrast with the first thin plate 1 of the first embodiment shown in FIG. 5 is formed so that the narrow horizontal portion 1a is supported by its middle portion by means of the vertical supporting portion 1b, the first and second thin plates 11 and 12 constituting the second embodiment are formed as follows. That is, a narrow horizontal portion 11a of the first thin plate 11 is supported by its one end (right end in FIG. 11) by means of a vertical supporting portion 11b so that an L shape is formed by the narrow horizontal portion 11a and vertical supporting portion 11b. Besides, the narrow horizontal portion 11a has a cut portion 11c at its free end. The shape of the second thin plate 12 is also the same as the shape of the first thin plate 11. The blood serum applicator according to the second embodiment is formed by combining the above-mentioned first and second thin plate 11 and 12 as described below. As shown in FIG. 9, the first and second thin plates 11 and 12 are combined face to face through a spacer 13 so that the vertical supporting portion 11b will not become directly opposed to the vertical supporting portion 12b and the first and second thin plates 11 and 12 and spacer 13 combined as above are fixed to a shank 15 by means of a screw 14.

To apply the blood serum onto the film by using the blood serum applicator constructed as above, it is only required to permeate the blood serum 17 into the groove 16 between the narrow horizontal portions 11a and 12a onto the film 18 in the same way as the case of the first embodiment. In case of the second embodiment, surplus blood serum does not gather at both ends of the groove 16 because the narrow horizontal portions 11a and 12a respectively have the cut portions 11c and 12c.

Figure 12:
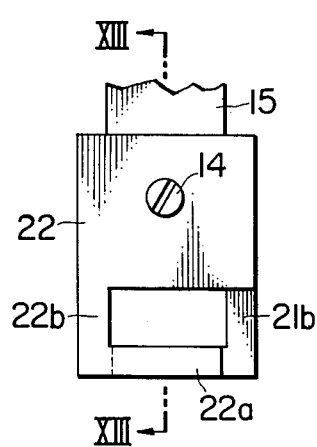
FIG. 12 shows a front view of a third embodiment of the present invention.
Figure 13:
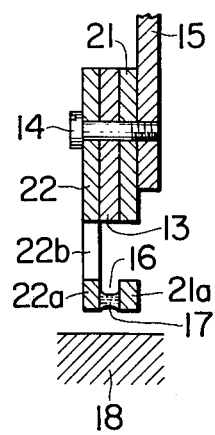
FIG. 13 shows a sectional view taken along the line XIII—XIII in FIG. 12.
Figure 14:
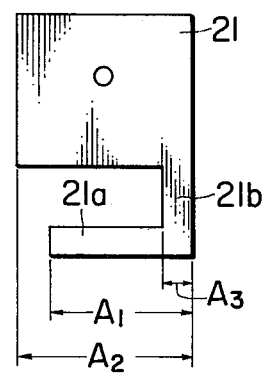
FIG. 14 shows a front view of a thin plate constituting the third embodiment.

A third embodiment of the blood serum applicator according to the present invention is shown in FIGS. 12 through 14. In the third embodiment, only the shape of thin plates is slightly different from the second embodiment as shown in FIG. 14 and the other arrangement is substantially the same as the second embodiment. In the above figures, numerals 21 and 22 respectively designate a first and second thin plates which are formed as described below. As shown in FIG. 14, the length $A_1$ of a narrow horizontal portion 21a of the first thin plate 21 is made smaller than the width $A_2$ of the first thin plate 21. The shape of the second thin plate 22 is also the same as the shape of the first thin plate 21. As the first and second thin plates 21 and 22 are formed as above, surplus blood serum does not gather at both ends of the groove formed between the narrow horizontal portions 21a and 22a.

In the third embodiment, it is preferable to arrange so that the narrow horizontal portion 21a of the first thin plate 21 does not overlap with the vertical supporting portion 22b of the second thin plate 22 and that the narrow horizontal portion 22a of the second thin plate 22 does not overlap with the vertical supporting portion 21b of the first thin plate 21 as shown in FIG. 12 when the blood serum applicator is assembled. Therefore, it is preferable to make the dimension $A_1$ in FIG. 14 shorter than $A_2-A_3$.

As explained in the above, the present invention provides a blood serum applicator by which it is possible to apply the blood serum onto the film uniformly and linearly and, moreover, to apply the blood serum accurately and quickly. Especially, by the blood serum applicator according to the second and third embodiments, it is possible to apply the blood serum onto the film more favourably because surplus blood serum does not gather at both ends of the groove when the blood serum is permeated into the groove.

I claim:
1. A blood serum applicator, comprising:
a first vertically short, laterally thin, longitudinally long horizontal plate-like straight portion having a flat lower edge which extends from one end thereof to an opposite end thereof;
a second vertically short, laterally thin, longitudinally long horizontal plate-like straight portion having a flat lower edge which extends from one end thereof to an opposite end thereof;
said first and second straight portions being disposed laterally adjacent one another with a constant-width space therebetween and said flat lower edges at an equal level;
main body means space vertically above said first and second straight portions;
a first, one vertically tall, laterally thin, longitudinally horizontally short plate-like supporting portion fixedly integrated with said first straight portion and with said main body means, and constituting the sole means mounting the first straight portion to said main body means;
a second, at least one and no more than two vertically tall, laterally thin, longitudinally horizontally short plate-like supporting portion fixedly integrated with said second straight portion and with said main body means, and constituting the sole means mounting the second straight portion to said main body means;
no part of said first, one supporting portion laterally confronting any part of said second at least one supporting portion, so that blood serum, when carried in said constant width space has no part thereof carried between said first, one supporting portion and said second at least one supporting portion.

2. A blood serum applicator, comprising:
a first thin plate having a main body, said first thin plate further having a narrow horizontal portion and a vertical supporting portion extending from intermediate the length of said narrow horizontal portion and connecting said narrow horizontal portion to said main body of said first thin plate;
a second thin plate having a main body, said second thin plate further having a narrow horizontal portion and two respective vertical supporting portions, respectively extending from opposite ends of said narrow horizontal portion and connecting said narrow horizontal portion to said main body of said second thin plate; and
a spacer;
said first and second thin plates being fixed to each other through said spacer so that said narrow horizontal portion of said first thin plate is arranged laterally adjacent to and parallel with said narrow horizontal portion of said second thin plate and;
said vertical supporting portion of said first thin plate is not laterally confronting any part of either of said two respective vertical supporting portions of said second thin plate, so that blood serum, when carried between said narrow horizontal portions has no part thereof carried between said vertical supporting portion of said first thin plate and either of said two respective vertical supporting portions of said second thin plate.

3. A blood serum applicator, comprising:

a first thin plate having a main body, said first thin plate further having a narrow horizontal portion and a vertical supporting portion extending from one end of said narrow horizontal portion and connecting said narrow horizontal portion to said main body of said first thin plate, said narrow horizontal portion having a cut portion at the opposite end thereof from said one end;

a second thin plate also having a main body, and further having a narrow horizontal portion and a vertical supporting portion extending from one end of said narrow horizontal portion of said second thin plate and connecting said narrow horizontal portion of said second thin plate to said main body of said second thin plate, said narrow horizontal portion of said second thin plate having a cut portion at the opposite end thereof from said one end thereof; and a spacer;

said first and second thin plates being fixed to each other said spacer so that said narrow horizontal portion of said first thin plate is arranged laterally adjacent to and parallel with said narrow horizontal portion of said second thin plate and said vertical supporting portion of said first thin plate is not directly opposed to said vertical supporting portion of said second thin plate;

so that blood serum when carried between said narrow horizontal portions has no part thereof carried between said vertical supporting portion of said first thin plate and said vertical supporting portion of said second thin plate.

4. A blood serum applicator according to claim 3, in which:

the horizontal length of said narrow horizontal portions of said first and second thin plates is smaller than the width, in the same direction, of said first and second thin plates.

5. A blood serum applicator according to claim 3, in which:

the horizontal length of said narrow horizontal portions of said first and second thin plates is smaller than the difference between the width, in the same direction, of said first and second thin plates and the width, in the same direction, of said vertical supporting portion.

* * * * *